US012799144B2

(12) United States Patent
Yeo et al.

(10) Patent No.: US 12,799,144 B2
(45) Date of Patent: Nov. 17, 2026

(54) BENZIMIDAZOLE DERIVATIVE COMPOUNDS AND USE THEREOF

(71) Applicant: PHARMGEN SCIENCE, INC., Hwaseong-si (KR)

(72) Inventors: Marie Yeo, Yongin-si (KR); JeDo Oh, Yongin-si (KR); SeulAe Lee, Seongnam-si (KR); SangHak Lee, Hwaseong-si (KR); HyeYoun Kim, Seoul (KR); HeeDeok Park, Hwaseong-si (KR); EuiSang Han, Seoul (KR); DongKyu Kim, Suwon-si (KR); DoHyung Lee, Suwon-si (KR); SeungHee Kang, Bucheon-si (KR)

(73) Assignee: PHARMGEN SCIENCE, INC., Hwaseong-si (KR)

( * ) Notice: Subject to any disclaimer, the term of this patent is extended or adjusted under 35 U.S.C. 154(b) by 315 days.

(21) Appl. No.: 18/717,626

(22) PCT Filed: Dec. 7, 2022

(86) PCT No.: PCT/KR2022/019846

§ 371 (c)(1),
(2) Date: Jun. 7, 2024

(87) PCT Pub. No.: WO2023/106841

PCT Pub. Date: Jun. 15, 2023

(65) Prior Publication Data

US 2025/0051376 A1 Feb. 13, 2025

(30) Foreign Application Priority Data

Dec. 8, 2021 (KR) ........................ 10-2021-0174301

(51) Int. Cl.
*C07F 9/6561* (2006.01)
*A61K 31/675* (2006.01)
*A61P 1/04* (2006.01)

(52) U.S. Cl.
CPC .......... *C07F 9/6561* (2013.01); *A61K 31/675* (2013.01); *A61P 1/04* (2018.01)

(58) Field of Classification Search
CPC ......... C07F 9/6561; A61P 1/04; A61K 31/675
USPC ........................................................... 514/81
See application file for complete search history.

(56) References Cited

U.S. PATENT DOCUMENTS

2008/0214519 A1 9/2008 Koike et al.

FOREIGN PATENT DOCUMENTS

JP 2008-543824 A 12/2008
KR 10-2020-0002739 A 1/2020

*Primary Examiner* — Kahsay Habte
(74) *Attorney, Agent, or Firm* — GOLDILOCKS ZONE IP LAW

(57) ABSTRACT

The invention relates to benzimidazole derivative compounds represented by Formula 1 or Formula 2 showing a gastric acid secretion inhibitory effect, a pharmaceutical composition comprising the compounds as an active ingredient, and the use thereof.

9 Claims, No Drawings

BENZIMIDAZOLE DERIVATIVE COMPOUNDS AND USE THEREOF

CROSS-REFERENCE TO RELATED APPLICATIONS

This application claims the benefit under 35 U.S.C. Section 371, of PCT International Application No. PCT/KR2022/019846, filed on Dec. 7, 2 02 2, which claimed priority to Korean Patent Applications No. 10-2021-0174301, filed on Dec. 8, 2021, in the Korean Intellectual Property Office, both of which are hereby incorporated by reference in their entireties.

TECHNICAL FIELD

The invention relates to a benzimidazole derivative compound and use thereof, more specifically to the following the benzimidazole derivative compound represented by Formula 1 or Formula 2, or a pharmaceutically acceptable salt thereof or a stereoisomer thereof and use thereof:

[Formula 1]

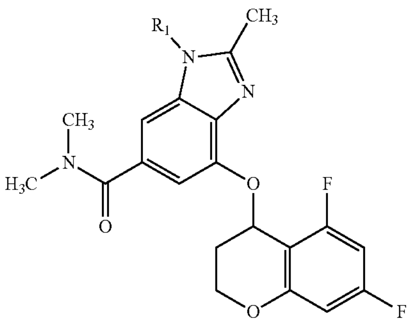

[Formula 2]

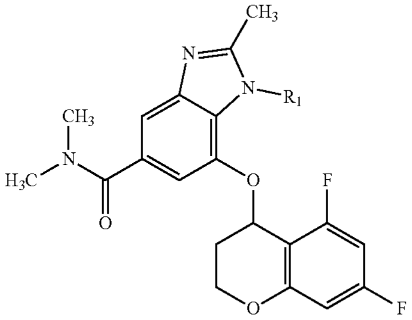

in the Formula above, wherein $R_1$ is the same as defined in the specification.

BACKGROUND ART

A gastric acid plays a positive role in digesting proteins, absorbing minerals such as calcium and iron, and sterilizing harmful microorganisms in ingested food. However, because gastric acid is a very strong acid with a pH of around 1 to 2, excessive gastric acid secretion or reflux into the esophagus can cause gastritis, gastric ulcers, and gastroesophageal reflux disease (GERD).

The gastric acid secretion is made with the proton pump (H+/K+-ATPase) of parietal cells existing in the gastric mucosa. Due to various gastric acid secretion stimulating factors, the proton pump consumes ATP and excretes hydrogen ions into the gastric cavity by exchanging hydrogen ions in the cytoplasm and potassium ions in the stomach lumen.

As drugs to suppress gastric acid secretion, H2 receptor blockers (H2 receptor antagonists, H2 RAs) and proton pump inhibitors (PPIs) have been commonly used. However, H2 RA does not directly inhibit the proton pump, but only blocks the histamine pathway that stimulates gastric acid secretion, so it has a partial effect. In addition, PPIs are prodrugs and must be taken before meals because they exert their effects after being activated by stomach acid, Because the onset of action is slow and the half-life is short, there are limitations in suppressing the symptoms of nocturnal acid breakthrough (NAB). Therefore, there is a need to develop drugs that inhibit gastric acid secretion with a new mechanism that can compensate for these shortcomings.

Recently, vonoprazan (Japan, 2015) and tegoprazan (Korea, 2019) were released as a new class of gastric acid suppressing drugs, P-CAB (potassium-competive acid blocker). P-CAB class drugs have a 5 to 100-fold improvement in the ability to inhibit the proton pump that secretes gastric acid compared to existing PPIs, demonstrating stronger efficacy than PPIs. In addition, in the mechanism of action, existing PPIs are precursors (prodrugs) and require an activation process in acid, but P-CAB does not require an activation process. In particular, while PPI has an irreversible covalent bond with the proton pump, P-CAB has the advantage of having a very fast onset time, a long duration of action, and being able to be taken regardless of diet by bonding reversibly.

However, among the P-CAB class drugs, tegoprazan (Korea, 2019) has pH-dependent water solubility and is a poorly soluble drug with significantly low solubility, especially in neutral aqueous solutions. Due to these characteristics, when the pH in the gastric cavity rises to neutral, such as during a meal, the solubility of the drug decreases, which reduces bioavailability and makes it difficult to formulate various formulations such as neutral injections.

DISCLOSURE

Technical Problem

The purpose of the present invention is to provide a novel benzimidazole derivative compound represented by Formula 1 or Formula 2 that exhibits gastric acid secretion inhibition activity.

Another object of the present invention is to provide a pharmaceutical composition for inhibiting gastric acid secretion, comprising the above compound as an active ingredient.

Another object of the present invention is to provide a pharmaceutical composition for preventing or treating diseases caused by gastric acid secretion disorders, comprising the above compound as an active ingredient.

Technical Solution

According to one aspect of the present invention, a benzimidazole derivative compound represented by Formula 1 or Formula 2, or a pharmaceutically acceptable salt thereof or a stereoisomer thereof provided:

[Formula 1]

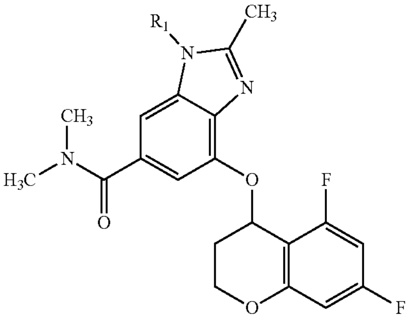

[Formula2]

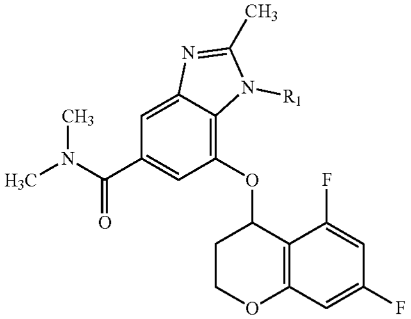

in the Formula above, wherein $R_1$ is 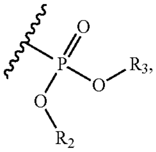 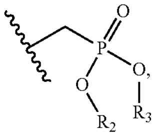 or

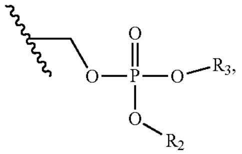

wherein $R_2$ and $R_3$ are each independently hydrogen, alkyl or cycloalkyl.

The benzimidazole derivative compound of Formula 1 or Formula 2 according to the present invention can form a pharmaceutically acceptable salt. The pharmaceutically acceptable salts may include, but are not limited to, alkali metal or alkaline earth metal salts formed by, for example, sodium, lithium, potassium, calcium, magnesium, etc. The benzimidazole derivative compound of Formula 1 or Formula 2 according to the present invention can be converted into its salt by a conventional method.

In the meantime, the compounds according to the present invention may have an asymmetric carbon center and therefore may exist as R or S isomers, racemates, diastereomeric mixtures and individual diastereomers, and all of these isomers and mixtures are included in the scope of the present invention.

In this specification, unless otherwise specified for convenience, the benzimidazole derivative compound of Formula 1 or Formula 2 is used to include the compound of Formula 1 or Formula 2, and pharmaceutically acceptable salts and stereoisomers thereof.

In defining the benzimidazole derivative compound of Formula 1 or Formula 2 throughout this specification, the following concepts defined for substituents are used.

Unless otherwise stated, the term "alkyl" herein refers to a radical the saturated aliphatic hydrocarbon group having the straight-chain or the branched, for example, the carbon atom of 1 to 7 in the present application. As an example of the alkyl group, methyl, ethyl, n-propyl, isopropyl, n-butyl, isobutyl, sec-butyl, tert-butyl, n-pentyl, isopentyl, neopentyl, tert-pentyl, 1-methylbuthyl, 2-methylbuthyl, 1-ethylpropyl and 1,2-dimethylpropyl etc. are included but it is not limited thereto.

Unless otherwise stated, the term "cycloalkyl" herein refers to a radical of the group of cyclic, for example, saturated aliphatic hydrocarbons having 3 to 7 carbon atoms. As an example of the cycloalkyl group, cyclopropyl, cyclobutyl, cyclopentyl, cyclohexyl etc is included but it is not limited thereto.

According to one embodiment of the invention, in Formula 1 or Formula 2, $R_2$ and $R_3$ may each independently be hydrogen, $C_1$-$C_7$ alkyl or $C_3$-$C_7$ cycloalkyl.

According to another embodiment of the present invention, in Formula 1 or Formula 2, $R_2$ and $R_3$ may each independently be hydrogen or $C_1$-$C_5$ alkyl.

Representative benzimidazole derivative compounds of Formula 1 or Formula 2 according to the present invention may include, but are not limited to, the following compounds:

diisopropyl(S)-(4-((5,7-difluorochroman-4-yl)oxy)-6-(dimethylcarbamoyl)-2-methyl-1H-benzo[d]imidazol-1-yl) phosphonate;

(S)-di-tert-butyl ((4-((5,7-difluorochroman-4-yl)oxy)-6-(dimethylcarbamoyl)-2-methyl-1H-benzo[d]imidazol-1-yl) methyl)phosphate;

tert-butyl ((4-(((S)-5,7-difluorochroman-4-yl)oxy)-6-(dimethylcarbamoyl)-2-methyl-1H-benzo[d]imidazol-1-yl) methyl) hydrogen phosphate;

(S)-(4-((5,7-difluorochroman-4-yl)oxy)-6-(dimethylcarbamoyl)-2-methyl-1H-benzo[d]imidazol-1-yl)methyl dihydrogen phosphate;

sodium(S)-tert-butyl ((4-((5,7-difluorochroman-4-yl)oxy)-6-(dimethylcarbamoyl)-2-methyl-1H-benzo[d]imidazol-1-yl)methyl)phosphate;

sodium(S)-(4-((5,7-difluorochroman-4-yl)oxy)-6-(dimethylcarbamoyl)-2-methyl-1H-benzo[d]imidazol-1-yl) methyl phosphate.

According to another aspect of the present invention, a pharmaceutical composition for the inhibition of gastric acid secretion comprising the benzimidazole derivative compound of the Formula 1 or Formula 2, or a pharmaceutically acceptable salt thereof or a stereoisomer thereof as an active ingredient, with a pharmaceutically acceptable carrier provided.

According to another aspect of the present invention, a pharmaceutical composition for the preventing or treating diseases caused by disorders of gastric acid secretion comprising the benzimidazole derivative compound of the Formula 1 or Formula 2, or a pharmaceutically acceptable salt thereof or a stereoisomer thereof as an active ingredient, with a pharmaceutically acceptable carrier provided.

In the present invention, "pharmaceutical composition" may include other chemical components such as carriers, diluents, excipients, etc. in addition to the active compound according to the present invention. Accordingly, the pharmaceutical composition may include a pharmaceutically acceptable carrier, diluent, excipient, or a combination thereof, if necessary.

According to another embodiment of the present invention, the diseases caused by gastric acid secretion disorders include gastrointestinal diseases, gastroesophageal diseases, gastroesophageal reflux disease (GERD), peptic ulcers, gastric ulcers, duodenal ulcers, NSAID-induced ulcers, gastritis, and Helicobacter pylori. Helicobacter pylori infection, indigestion, functional dyspepsia, Zollinger-Ellison syndrome, non-erosive reflux disease (NERD), visceral pain, heartburn, nausea, esophagitis, dysphagia, drooling, airway disorder, or asthma, but is not limited thereto.

Advantageous Effects

Since the benzimidazole derivative compound represented by Formula 1 or Formula 2 according to the present invention exhibits an effect of suppressing gastric acid secretion, it can function as a potassium-competitive acid blocker (P-CAB) and inhibits gastric acid secretion. It can be used as a secretion inhibitor or as a preventive or treatment agent for diseases caused by gastric acid secretion disorders. In addition, the benzimidazole derivative compound represented by Formula 1 or Formula 2 according to the present invention has significantly improved neutral water solubility than tegoprazan, which was previously developed as a gastric acid suppressing drug, and is not affected by pH in vivo, such as diet, and it is facilitated in the formulation including the injection agent.

MODE FOR CARRYING OUT THE INVENTION

Hereinafter, the present invention will be described in more detail through preparation examples and examples. However, these examples are only illustrative of the present invention, and the scope of the present invention is not limited thereto.

An explanation of the abbreviations used in the examples below is as follows:

ACN: acetonitrile.

DMF: N,N-dimethylformamid.

EtOAc: ethyl acetate.

FA: formic acid

MeOH: methanol.

Embodiment 1: Synthesis of diisopropyl(S)-(4-((5,7-difluorochroman-4-yl)oxy)-6-(dimethylcarbamoyl)-2-methyl-1H-benzo (d) imidazol-1-yl)phosphonate

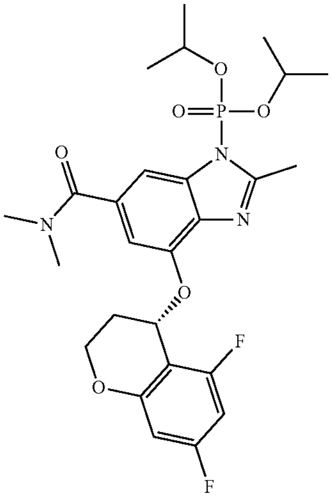 [SMILES: Cc1nc2c(O[C@H]3CCOc4cc(F)cc(F)c43)cc(C(=O)N(C)C)cc2n1P(=O)(OC(C)C)OC(C)C]

7-[(4S)-5,7-difluoro-3,4-dihydro-2H-chromen-4-yl]oxy]-N,N,2-trimethyl-3H-benzimidazole-5-Carboxamide (80 mg, 0.21 mmol) was dissolved in dry DMF (2 mL), and then 60% NaH (12.39 mg, 0.31 mmol) was added at 0 °C under a nitrogen atmosphere and stirred at room temperature for 30 minutes. Diisopropyl phosphorochloridate (53.85 mg, 0.27 mmol) was added to this reaction at 0 °C and stirred at room temperature for 1 hour. After completion of the reaction, it was extracted with EtOAc, washed with brine, dried with anhydrous Na2SO4, and separated by column chromatography (EtOAc:Hexane:MeOH=6:6:1) to obtain the target compound, diisopropyl(S)-(4-((5,7-difluorochroman-4-yl)oxy)-6-(dimethylcarbamoyl)-2-methyl-1H-benzo[d]imidazole-1-yl)phosphonate (43 mg, 37%) as a white solid.

NMR (DMSO-d6): 7.13 (1H), 6.93 (s, 1H), 6.83 (t, 1H), 6.70 (d, 1H), 6.03 (s, 1H), 4.43~4.37 (m, 3H), 4.25 (t, 1H), 2.97 (s, 6H), 2.45 (s, 3H), 2.24 (d, 1H), 2.07 (t, 1H), 1.24 (d, 12H); MS+: 552.44

Embodiment 2: Synthesis of(S)-di-tert-butyl ((4-((5,7-difluorochroman-4-yl)oxy)-6-(dimethylcarbamoyl)-2-methyl-1H-benzo[d]imidazol-1-yl)methyl) phosphate

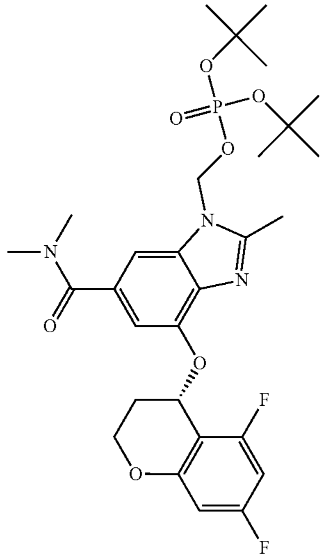 [SMILES: Cc1nc2c(O[C@H]3CCOc4cc(F)cc(F)c43)cc(C(=O)N(C)C)cc2n1COP(=O)(OC(C)(C)C)OC(C)(C)C]

7-[(4S)-5,7-difluoro-3,4-dihydro-2H-chromen-4-yl]oxy]-N, N,2-trimethyl-3H-benzimidazole-5-Carboxamide (1,000 mg, 2.58 mmol) was dissolved in dry DMF (25.8 mL), and then 60% NaH (154.89 mg, 3.87 mmol) was added at 0 °C under a nitrogen atmosphere and stirred at room temperature for 30 minutes. Diisopropyl phosphorochloridate (1,336 mg, 5.16 mmol) was added to this reaction at 0 °C and stirred at room temperature for 1 hour. After completion of the reaction, it was extracted with EtOAc, washed with brine, dried with anhydrous $Na_2SO_4$, and separated by column chromatography (EtOAc:Hexane:MeOH=6:6:1) to obtain the target compound, (S)-di-tert-butyl (4-((5,7-difluorochroman-4-yl)oxy)-6-(dimethylcarbamoyl)-2-methyl-1H-benzo[d]imidazol-1-yl)methyl)Phosphate (812 mg, 52%) was obtained as a white solid.

NMR (DMSO-d6): 7.30 (s, 1H), 6.94 (s, 1H), 6.81 (t, 1H), 6.76 (d, 1H), 6.14 (s, 1H), 6.02 (d, 2H), 4.36 (d, 1H), 4.22 (d, 1H), 2.97 (s, 6H), 2.61 (s, 3H), 2.22 (d, 1H), 2.07 (t, 1H), 1.38~1.26 (m, 18H); MS+: 610.33

Embodiment 3: Synthesis of tert-butyl ((4-(((S)-5,7-difluorochroman-4-yl)oxy)-6-(dimethylcarbamoyl)-2-methyl-1H-benzo (d) imidazol-1-yl)methyl) hydrogen phosphate

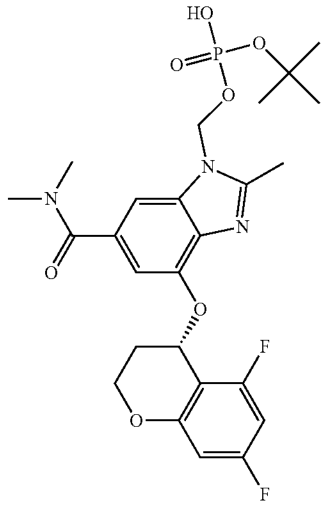 [SMILES: Cc1nc2c(O[C@H]3CCOc4cc(F)cc(F)c43)cc(C(=O)N(C)C)cc2n1COP(=O)(O)OC(C)(C)C]

(S)-di-tert-butyl (4-((5,7-difluorochroman-4-yl)oxy)-6-(dimethylcarbamoyl)-2-methyl-1H-benzo[d] Imidazol-1-yl) methyl)phosphate (295 mg, 0.49 mmol) was dissolved in dry DMF (4.86 mL), and then 4N HCl (1.4 mL) was added at 0 °C and stirred at room temperature for 90 minutes. After completion of the reaction, it was separated by reversed-phase column chromatography (0.1% FA) and freeze-dried, to obtain the target compound, tert-butyl ((4-(S)-5,7-difluorochroman-4-yl)oxy-6-(dimethylcarbamoyl)-2-methyl-1H-benzo[d]imidazol-1-yl)methyl) hydrogen phosphate (74.2 mg, 27%) was obtained as a white solid.

NMR (DMSO-d6): 7.31 (s, 1H), 6.94 (s, 1H), 6.81 (t, 1H), 6.71 (d, 1H), 6.15 (s, 1H), 5.96 (d, 2H), 4.37 (d, 1H), 4.23 (t, 1H), 2.98 (s, 6H), 2.64 (s, 3H), 2.24 (d, 1H), 2.07 (m, 1H), 1.26 (s, 9H); MS+: 554.47

Embodiment 4: Synthesis of(S)-(4-((5,7-difluorochroman-4-yl)oxy)-6-(dimethylcarbamoyl)-2-methyl-1H-benzo[d]imidazol-1-yl)methyl dehydrogen phosphate

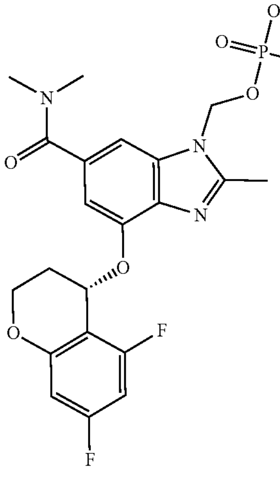

Tert-butyl ((4-(S)-5,7-difluorochroman-4-yl)oxy)-6-(dimethylcarbamoyl)-2-methyl-1H-benzo[d]imidazole-1-yl) methyl) hydrogen phosphate (200 mg, 0.33 mmol) was dissolved in DMF (6.57 mL), then 4N HCl (0.5 mL) was added at 0 °C and stirred at room temperature for 90 minutes. After completion of the reaction, it was separated by reverse-phase column chromatography (0.1% FA) and lyophilized to obtain the target compound, (S)-(4-((5,7-difluorochroman-4-yl)oxy)-6-(dimethylcarbamoyl)-2-methyl-1H-benzo[d]imidazol-1-yl)methyl dihydrogen phosphate (64.1 mg, 35%) was obtained as a white solid.

NMR (DMSO-d6): 7.31 (s, 1H), 6.94 (s, 1H), 6.81 (t, 1H), 6.71 (d, 1H), 6.14 (s, 1H), 5.95 (d, 2H), 4.37 (d, 1H), 4.22 (t, 1H), 2.98 (s, 6H), 2.64 (d, 3H), 2.25 (d, 1H), 2.07 (m, 1H); MS+: 498.29

Embodiment 5: Synthesis of sodium(S)-tert-butyl ((4-((5,7-difluorochroman-4-yl)oxy)-6-(dimethylcarbamoyl)-2-methyl-1H-benzo (d) imidazol-1-yl) methyl)phosphate)

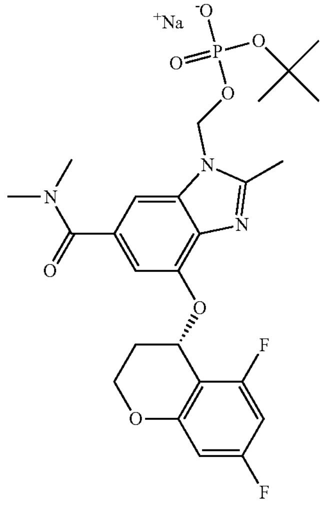

Tert-butyl ((4-(S)-5,7-difluorochroman-4-yl)oxy)-6-(dimethylcarbamoyl)-2-methyl-1H-benzo[d]imidazole-1-yl) methyl) hydrogen phosphate (52.8 mg, 0.095 mmol) was dissolved in ACN:$H_2O$=1:1 (9.5 mL), then NaOH (4.2 mg, 0.105 mmol) was added and stirred at room temperature for 1 minute. After completion of the reaction, it was lyophilized to obtain the target compound, sodium(S)-tert-butyl (4-((5,7-difluorochroman-4-yl)oxy)-6-(dimethylcarbamoyl)-2-Methyl-1H-benzo[d]imidazol-1-yl)methyl)phosphate (54 mg, 98%) was obtained as a white solid.

NMR (D2O): 7.47 (s, 1H), 7.13 (s, 1H), 6.65~6.56 (m, 2H), 5.96~5.93 (m, 3H), 4.51~4.45 (m, 2H), 3.15 (s, 3H), 3.05 (s, 3H), 2.72 (s, 3H), 2.39 (d, 1H), 2.22~2.14 (m, 1H), 1.04 (s, 9H); MS+: 554.35

Embodiment 6: Synthesis of sodium(S)-(4-((5,7-difluorochroman-4-yl)oxy)-6-(dimethylcarbamoyl)-2-methyl-1H-benzo (d) imidazol-1-yl)methyl phosphate)

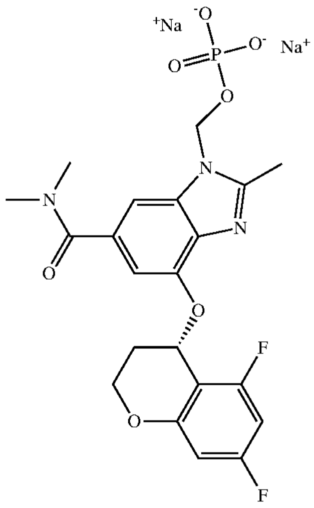

(S)-(4-((5,7-difluorochroman-4-yl)oxy)-6-(dimethylcarbamoyl)-2-methyl-1H-benzo[d]imidazole-1-1)methyl dihydrogen phosphate (51.6 mg, 0.104 mmol) was dissolved in ACN: H2O=1:1 (10.4 mL), then NaOH (8.7 mg, 0.218 mmol) was added and stirred at room temperature for 1 minute. After completion of the reaction, it was lyophilized to obtain the target compound, sodium(S)-(4-((5,7-difluorochroman-4-yl)oxy)-6-(dimethylcarbamoyl)-2-methyl-1H-benzo[d]imidazol-1-yl)methyl phosphate (52 mg, 93%) was obtained as a white solid.

NMR (D2O): 7.52 (s, 1H), 7.11 (s, 1H), 6.65~6.58 (m, 2H), 5.95 (s, 1H), 5.84 (d, 2H), 4.48~4.45 (m, 2H), 3.15 (s, 3H), 3.06 (s, 3H), 2.71 (s, 3H), 2.41 (d, 1H), 2.22~2.13 (m, 1H); MS+: 498.33

Experimental Example 1: Water Solubility Test (pH 6.8)

After it measured so that each testing material was concentrated by 5.12 mg/ml in the glass vial, 0.5M Tris-HCl (pH 6.8, T&I, BTH-9168) was added and it processed in for one minute mixing, and treated in a sonicator for 30 minutes the solution was prepared. The solution was observed with the naked eye and recorded in photographs. If it was not completely dissolved, additional buffer was added to prepare a solution and the observation was repeated. Solubility was evaluated by checking the concentration when completely dissolved. Tegoprazan was used as a comparison compound. The measured results are shown in Table 1 below.

TABLE 1

| Compound | Solubility, pH 6.8 ( mg/ml) |
|---|---|
| Comparison compound | 0.02 |
| Embodiment 1 | 0.01 |
| Embodiment 2 | 5.12 |
| Embodiment 3 | 2.56 |

TABLE 1-continued

| Compound | Solubility, pH 6.8 ( mg/ml) |
|---|---|
| Embodiment 4 | 2.56 |
| Embodiment 5 | 5.12 |
| Embodiment 6 | 5.12 |

As shown in Table 1, the compounds of Examples 3 and 4 according to the present invention showed 128 times improved water solubility (pH 6.8) compared to the comparative compounds, and Examples 2, 5, and The compound of Example 6 showed 256 times improved water solubility (pH 6.8) compared to the comparative compound. Therefore, the new benzimidazole derivative compound of the present invention, which has significantly improved water solubility, has no effect on solubility even when the pH in the gastric cavity increases due to diet, and furthermore, it can be easily formulated, including injections.

experimental example 2: gastric acid releasing suppression ability qualification test by the oral administration.

A week before the test, test animals (rats) were purchased and acclimatized. After acclimatization, food was removed the day before the test and fasting was performed for 24 hours using a fasting plate. The weight of each individual was measured, weight ranking was sequentially assigned to each group, and the average value of each group was randomly distributed so that the average value was evenly distributed. Test material (the embodiment compound and comparison compound) were used by dissolving them in 0.5% methylcellulose solution, and tegoprazan was used as a comparative compound. The prepared test material was orally administered to test animals at an amount of 3 mg/5 ml/kg, and 30 minutes later, inhalation anesthesia (3% isoflurane) was performed for 3 minutes using an inhalation anesthesia machine. After making a minimal incision in the upper abdomen about 1 cm below the left side of the sternum of an anesthetized test animal, the stomach was exposed, and the pyloric ring, which is the connection between the stomach and the duodenum, was ligated. The stomach and duodenum were restored to their original positions, and the laparotomy site was sutured well with surgical staplers. Histamine (7.5 mg/2.5 mL/head) was slowly administered subcutaneously to the back of the neck to promote gastric acid secretion. 3 hours after the surgery, the experimental animals were anesthetized with isoflurane and the stomach was removed through laparotomy. Gastric fluid obtained from the extracted stomach was transferred to a 15 ml conical tube, centrifuged at 5,000 rpm for 10 minutes, and only the supernatant was separated. 0.2 mL of the separated gastric fluid was diluted in 24.8 mL of distilled water to make a total dilution of 25 mL, and then 0.01N NaOH was added in small amounts to titrate until the pH reached 7. Efficacy was evaluated by calculating total acidity by combining the amount of gastric fluid and the amount of 0.01N NaOH required for titration.

$$\text{Total Acid output } (\mu\text{Eq}) = \frac{\text{mL of 0.01N NaOH} \times 0.01\text{N} \times 1000 \times \text{Total amount of the gastric juice}}{\text{Amount of the gastric juice taken for titration}}$$

The measured result was shown in the following table 2.

TABLE 2

| Compound | gastric acid releasing suppression ability (% INH, Mean ± SD) |
|---|---|
| Comparison compound | 100 ± 0.0 *** |
| Embodiment 1 | 99.7 ± 0.2 *** |
| Embodiment 2 | 26.8 ± 9.2 * |
| Embodiment 3 | 23.9 ± 3.3 * |
| Embodiment 4 | 100.0 ± 0.0 *** |
| Embodiment 5 | 12.7 ± 10.9 * |
| Embodiment 6 | 92.8 ± 4.8 *** |

*, *** $p < 0.05$, $p < 0.001$ (vs Excipient control)

As shown in the table 2, it was confirmed that the compounds of embodiments 1, 4, and 6 according to the present invention have the powerful gastric acid releasing suppression ability in the gastric acid secretion animal model.

experimental example 3: gastric acid releasing suppression ability qualification test by the administration in the duodenum.

A week before the test, test animals (rats) were purchased and acclimatized. After acclimatization, food was removed the day before the test and fasting was performed for 24 hours using a fasting plate. The weight of each individual was measured, weight ranking was sequentially assigned to each group, and the average value of each group was randomly distributed so that the average value was evenly distributed. Test material (the embodiment compound and comparison compound) were used by dissolving them in 0.5% methylcellulose solution, and tegoprazan was used as a comparative compound. Experimental animals were subjected to inhalation anesthesia (3% isoflurane) for 3 minutes using an inhalation anesthesia machine. After making a minimal incision in the upper abdomen about 1 cm below the left side of the sternum of an anesthetized test animal, the stomach was exposed, and the pyloric ring, which is the connection between the stomach and the duodenum, was ligated. The prepared drug was administered into the duodenum in an amount of 1 mg/5 ml/kg, the stomach and duodenum were restored to their original positions, and the laparotomy site was sutured well with a surgical stapler. Histamine (7.5 mg/2.5 mL/head) was slowly administered subcutaneously to the back of the neck to promote gastric acid secretion. 3 hours after the surgery, the experimental animals were anesthetized with isoflurane and the stomach was removed through laparotomy. Gastric fluid obtained from the extracted stomach was transferred to a 15 ml conical tube, centrifuged at 5,000 rpm for 10 minutes, and only the supernatant was separated. 0.2 mL of the separated gastric fluid was diluted in 24.8 mL of distilled water to make a total dilution of 25 mL, and then 0.01N NaOH was added in small amounts to titrate until the pH reached 7. Efficacy was evaluated by calculating total acidity by combining the amount of gastric fluid and the amount of 0.01N NaOH required for titration.

$$\text{Total Acid output } (\mu\text{Eq}) = \frac{\text{mL of } 0.01\text{N NaOH} \times 0.01\text{N} \times 1000 \times \text{Total amount of the gastric juice}}{\text{Amount of the gastric juice taken for titration}}$$

The measured result was shown in the following table 3.

TABLE 3

| Compound | gastric acid releasing suppression ability (% INH, Mean ± SD) |
|---|---|
| Comparison compound | 29.8 ± 9.1 |
| Embodiment 6 | 43.7 ± 8.7 * |

* $p < 0.05$ (vs Excipient control)

As shown in the table 3, the compound of embodiment 6 according to the present invention showed an improved ability to inhibit gastric acid secretion compared to the comparative compound when the drug was administered to the duodenum with a neutral pH. Therefore, the compound of embodiment 6 according to the present invention is expected to exert the same effect regardless of pH even after a meal or in various biological environments in which the pH in the stomach cavity is neutral.

The invention claimed is:

1. A benzimidazole compound represented by Formula 1 or Formula 2, or a pharmaceutically acceptable salt thereof or a stereoisomer thereof:

[Formula 1]

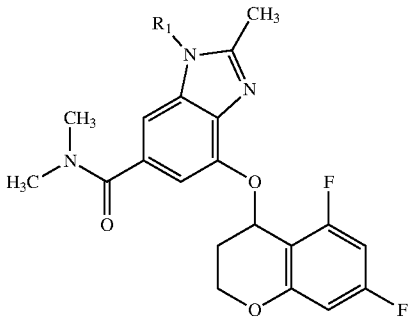

[Formula 2]

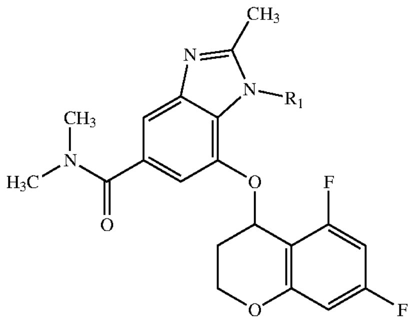

in the Formula above, wherein $R_1$ is

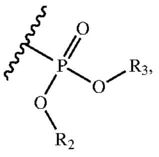

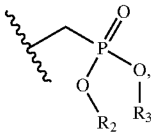

or

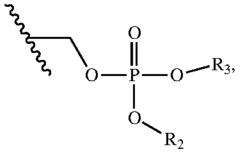

wherein $R_2$ and $R_3$ are each independently hydrogen, alkyl or cycloalkyl.

2. The benzimidazole compound, or a pharmaceutically acceptable salt thereof or a stereoisomer thereof according to claim 1, wherein $R_2$ and $R_3$ are each independently hydrogen, C1-C7 alkyl or C3-C7 cycloalkyl.

3. The benzimidazole compound, or a pharmaceutically acceptable salt thereof or a stereoisomer thereof according to claim 1, wherein $R_2$ and $R_3$ are each independently hydrogen, or C1-C5 alkyl.

4. The benzimidazole compound, or a pharmaceutically acceptable salt thereof or a stereoisomer thereof according to claim 1, wherein the pharmaceutically acceptable salt is alkali metal or alkaline-earth metal salt selected from the group consisting of sodium, lithium, potassium, calcium and magnesium.

5. The benzimidazole compound, or a pharmaceutically acceptable salt thereof or a stereoisomer thereof according to claim 4, wherein the pharmaceutically acceptable salt is sodium salt.

6. The benzimidazole compound, or a pharmaceutically acceptable salt thereof or a stereoisomer thereof according to claim 1, wherein the benzimidazole compound represented by Formula 1 or Formula 2 is selected from the following compounds:

diisopropyl(S)-(4-((5,7-difluorochroman-4-yl)oxy)-6-(dimethylcarbamoyl)-2-methyl-1H-benzo[d]imidazol-1-yl)phosphonate;

(S)-di-tert-butyl ((4-((5,7-difluorochroman-4-yl)oxy)-6-(dimethylcarbamoyl)-2-methyl-1H-benzo[d]imidazol-1-yl)methyl)phosphate;

tert-butyl ((4-(((S)-5,7-difluorochroman-4-yl)oxy)-6-(dimethylcarbamoyl)-2-methyl-1H-benzo[d]imidazol-1-yl)methyl) hydrogen phosphate;

(S)-(4-((5,7-difluorochroman-4-yl)oxy)-6-(dimethylcarbamoyl)-2-methyl-1H-benzo[d]imidazol-1-yl)methyl dihydrogen phosphate;

sodium(S)-tert-butyl ((4-((5,7-difluorochroman-4-yl)oxy)-6-(dimethylcarbamoyl)-2-methyl-1H-benzo[d]imidazol-1-yl)methyl)phosphate; and sodium(S)-(4-((5,7-difluorochroman-4-yl)oxy)-6-(dimethylcarbamoyl)-2-methyl-1H-benzo[d]imidazol-1-yl)methyl phosphate.

7. A pharmaceutical composition comprising the benzimidazole compound, or a pharmaceutically acceptable salt thereof or a stereoisomer thereof according to claim 1 as an active ingredient and a pharmaceutically acceptable carrier.

8. The pharmaceutical composition according to claim 7, wherein the active ingredient is present in an amount effective to reduce or suppress gastric acid secretion.

9. The pharmaceutical composition of claim 8, wherein the active ingredient is present in an amount therapeutical effective to treat a disease selected from the group consisting of gastroesophageal reflux disease (GERD), peptic ulcer, gastric ulcer, duodenal ulcer, NSAID-induced ulcer, gastritis dyspepsia, functional dyspepsia, Zollinger-Ellison syndrome, non-erosive reflux disease (NERD), and esophagitis.

* * * * *